US009084553B2

(12) United States Patent
Warmuth

(10) Patent No.: US 9,084,553 B2
(45) Date of Patent: Jul. 21, 2015

(54) HEART IMAGING WITH ADAPTIVE INVERSION TIME

(75) Inventor: Carsten Warmuth, Berlin (DE)

(73) Assignee: Siemens Aktiengesellschaft, Munich (DE)

( * ) Notice: Subject to any disclaimer, the term of this patent is extended or adjusted under 35 U.S.C. 154(b) by 1831 days.

(21) Appl. No.: 12/060,927

(22) Filed: Apr. 2, 2008

(65) Prior Publication Data

US 2008/0242973 A1   Oct. 2, 2008

(30) Foreign Application Priority Data

Apr. 2, 2007 (DE) .......................... 10 2007 015 928
Apr. 17, 2007 (DE) .......................... 10 2007 018 089

(51) Int. Cl.
| A61B 5/05 | (2006.01) |
| A61B 5/055 | (2006.01) |
| G01R 33/56 | (2006.01) |
| A61B 5/0456 | (2006.01) |
| A61B 5/00 | (2006.01) |
| G01R 33/563 | (2006.01) |
| G01R 33/565 | (2006.01) |
| G01R 33/567 | (2006.01) |

(52) U.S. Cl.
CPC ............ A61B 5/055 (2013.01); G01R 33/5601 (2013.01); G01R 33/5602 (2013.01); G01R 33/5607 (2013.01); A61B 5/0456 (2013.01); A61B 5/7285 (2013.01); G01R 33/5635 (2013.01); G01R 33/5673 (2013.01); G01R 33/56509 (2013.01)

(58) Field of Classification Search
CPC .. A61B 5/7285; A61B 5/7289; A61B 5/7292; G01R 33/5602; G01R 33/56509; G01R 33/5601; G01R 33/563; G01R 33/50; G01R 33/5615; G01R 33/5616; G01R 33/56536
USPC .................................. 600/410, 412, 413, 431
See application file for complete search history.

(56) References Cited

U.S. PATENT DOCUMENTS

| 5,429,134 A | 7/1995 | Foo |
| 5,545,992 A | 8/1996 | Foo |
| 5,908,386 A | 6/1999 | Ugurbil et al. |
| 2002/0087067 A1 | 7/2002 | Foo |
| 2003/0042905 A1* | 3/2003 | Miyazaki et al. ............. 324/314 |
| 2004/0049106 A1 | 3/2004 | Kanazawa |

(Continued)

FOREIGN PATENT DOCUMENTS

| EP | 1 593 984 A1 | 11/2005 |
| EP | 1593984 A1 * | 11/2005 |
| JP | 2004024637 A | 1/2004 |

OTHER PUBLICATIONS

Kim et al., Journal of Cardiovascular Magnetic Resonance vol. 5, No. 3, pp. 505-514, 2003.*

(Continued)

Primary Examiner — Long V Le
Assistant Examiner — Ellsworth Weatherby
(74) Attorney, Agent, or Firm — Schiff Hardin LLP

(57) ABSTRACT

In a method for acquisition of magnetic resonance images of the heart, MR signals of the heart are acquired using an imaging sequence, wherein the magnetization is inverted by an RF inversion pulse before the acquisition of the MR signals; and of the heart activity is detected, and the point in time of the switching of the RF inversion pulse dependent on the detected heart activity.

7 Claims, 2 Drawing Sheets

(56) References Cited

U.S. PATENT DOCUMENTS

| 2005/0245812 | A1* | 11/2005 | Kim et al. | 600/410 |
| 2005/0272997 | A1* | 12/2005 | Grist et al. | 600/410 |
| 2006/0094952 | A1* | 5/2006 | Ma et al. | 600/410 |
| 2006/0161060 | A1* | 7/2006 | Pai | 600/431 |
| 2007/0038069 | A1* | 2/2007 | Itagaki et al. | 600/410 |
| 2007/0249929 | A1* | 10/2007 | Jeong et al. | 600/410 |

OTHER PUBLICATIONS

"Ultrafast Magnetic Resonance Imaging Procedures for the Assessment of Cardiac Function," Spiegel, Dissertation for Swiss Federal Institute of Technology (2000).

* cited by examiner

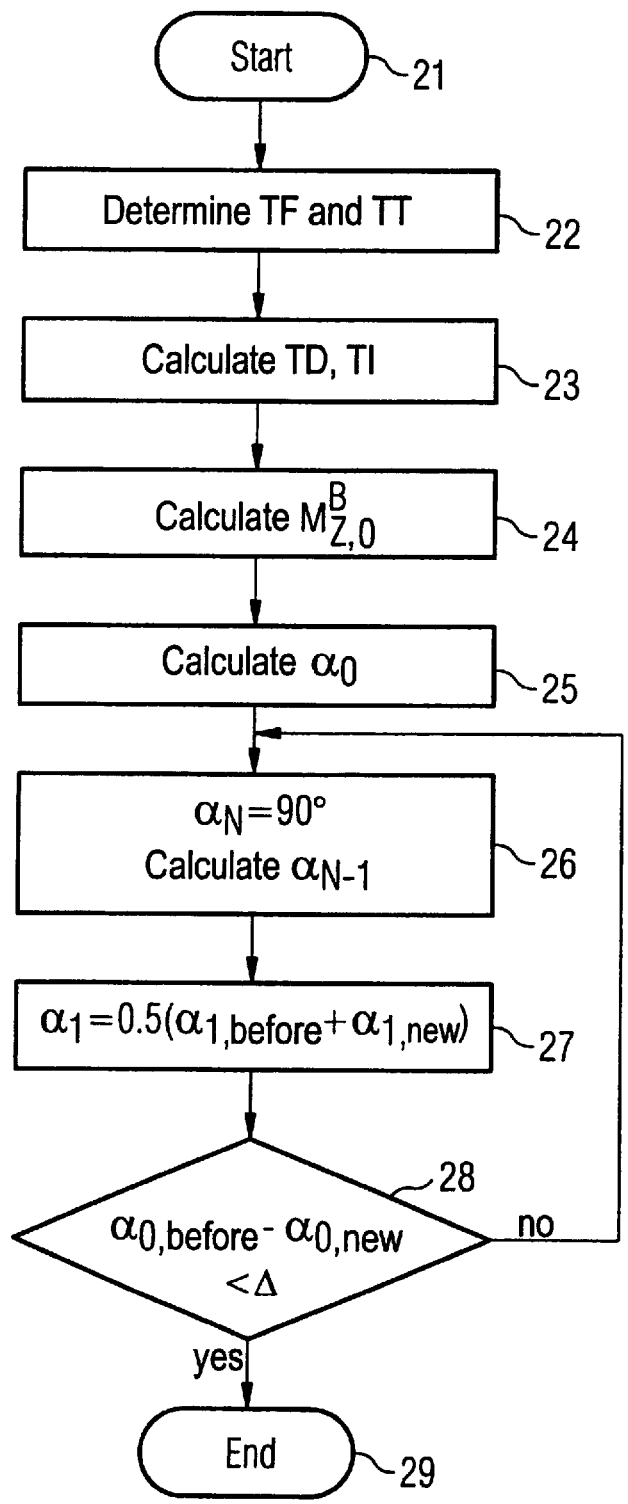

HEART IMAGING WITH ADAPTIVE INVERSION TIME

BACKGROUND OF THE INVENTION

1. Field of the Invention

The present invention concerns a method for acquisition of magnetic resonance images of the heart. The invention is in particular suited for use in imaging methods in which contrast agent is injected into the body in order to be able to intensify the contrast in the image of the heart.

2. Description of the Prior Art

Usually, in contrast agent-intensified heart imaging, an RF inversion pulse is emitted before the imaging in order to invert the magnetization by 180 degrees from the equilibrium state (steady state). Since the contrast agent in the blood significantly shortens the T1 relaxation time, an intensified contrast can be achieved between the blood in the heart and the myocardium. In known imaging methods of the heart, most imaging parameters are unalterable, once. Changes of the heart rate or the relaxation times of the tissue of interest have previously not been taken into account during the execution of the imaging sequence. The T1 relaxation time of the tissue (such as, for example, the myocardium) surrounding the bloodstream also changes, particularly in measurements of longer duration using contrast agent. The contrast ratio shown in the image is thereby degraded. In other applications a measurement according to the prior art is not reasonable at all since the T1 time change occurring over a longer time span no longer allows reasonable diagnostic conclusions.

SUMMARY OF THE INVENTION

An object of the present invention is to improve the contrast in inversion-prepared imaging methods with contrast agent and/or to make the measurement (data acquisition) possible over a longer time period.

This object is achieved according to the invention by a method for acquisition of magnetic resonance images of the heart, wherein the MR signals of the heart are acquired using an imaging sequence, in which the magnetization is inverted by an RF inversion pulse before acquisition of the MR signals, and wherein the heart activity of the examined person is detected or monitored. According to the invention, the point in time of the switching of the RF inversion pulse is selected dependent on the detected heart activity. Upon execution of the imaging sequence a maximum measurement signal and the optimal contrast between two tissues is achieved by taking into account the change of the heart rate. The inventive method leads to higher-contrast exposures, particularly for longer measurements using contrast agents.

In an embodiment of the invention, the point in time for switching of the RF inversion pulse is adapted before the imaging so that the longitudinal magnetization of the myocardium is minimized in the signal acquisition, wherein the time span TI from the inversion pulse until the beginning of the signal acquisition is varied. Via the variation of the point in time at which the inversion pulse is switched, it can be ensured that the data acquisition always ensues at a point in time at which the longitudinal magnetization of the myocardium is minimal, even given varying T1 relaxation time of the myocardium or given a change of the heart rate. If this is achieved, the signal contributions from the myocardium in the image are always low, meaning that the myocardium appears dark, independent of the possibly altered T1 relaxation time of the myocardium tissue or an altered heart rate. The imaging always ensues at a point in time at which the myocardium delivers low signal portions.

Furthermore, the imaging sequence can be a segmented imaging sequence in which only a portion of k-space (raw data space) is acquired during a heart cycle. In the imaging of the heart the short rest phase of the heart in the heart cycle must be determined, and the imaging must be adapted so that the MR signals are acquired during the rest position of the heart. In this short time it is normally not possible to fill the entire raw data space. For this reason, in an embodiment of the invention segmented imaging sequences are used in which (for example) only a small portion of the raw data space is acquired during a specific time span of the heart cycles.

The imaging sequence is advantageously a gradient echo-based imaging sequence in which the MR signals are acquired using bipolar rephased gradients. Various gradient echo sequences that can be used in the present invention are known. The invention is not limited to gradient echo-based imaging sequences. It is also possible to use a (turbo) spin echo sequence as the imaging sequence.

Advantageously, only N RF excitation pulses are switched (emitted) during a heart beat given the segmented acquisition of k-space. Furthermore, a pulse known as a spoiler is advantageously used after each RF excitation pulse, this spoiler destroying the remaining transverse magnetization before the next excitation pulse. These various N excitation pulses are repeated at different heart cycles until the entire raw data space is filled with data. The heart activity is typically detected in that the electrocardiogram (EKG) of the examination person is detected. A pattern that occurs in the EKG is the R-spike (R-wave) in the heart cycle. In an embodiment of the invention, the time span TF from the acquisition of the MR signals to the R-spike of the heart cycle can be determined for at least one preceding heart cycle. The time span TT from the R-spike of the heart cycle until the beginning of the acquisition of the MR signals can likewise be established, or the time span TT is selected dependent on the expected R-spike interval RR. The time span TD from the R-spike until the switching of the RF inversion pulse can subsequently be calculated on the basis of the variables TT and TF. This time span TD specifies when the RF inversion pulse is radiated after the detection of the R-spike. In am embodiment of the invention, this time span TD is calculated dependent on values previously acquired during the imaging. The point in time of switching the RF inversion pulse is calculated and adapted during the run time of the imaging sequence.

The longitudinal magnetization of the blood $M_{z,0}^B$ is calculated in a further step. According to a further embodiment of the invention, the flip angle $\alpha$ of the RF inversion pulse can be varied so that the measurement signal is essentially constant upon acquisition of the MR signals via the N excitation pulses. The flip angle can be varied so that a flip angle of 90 degrees is established for the Nth excitation pulse while the flip angles of N−1 through 1 are calculated from the Nth flip angle in an iteration procedure.

BRIEF DESCRIPTION OF THE DRAWINGS

FIG. 2 is a flowchart of an embodiment of the inventive method steps for calculation of the sequence parameters.

DESCRIPTION OF THE PREFERRED EMBODIMENTS

Figure 1:
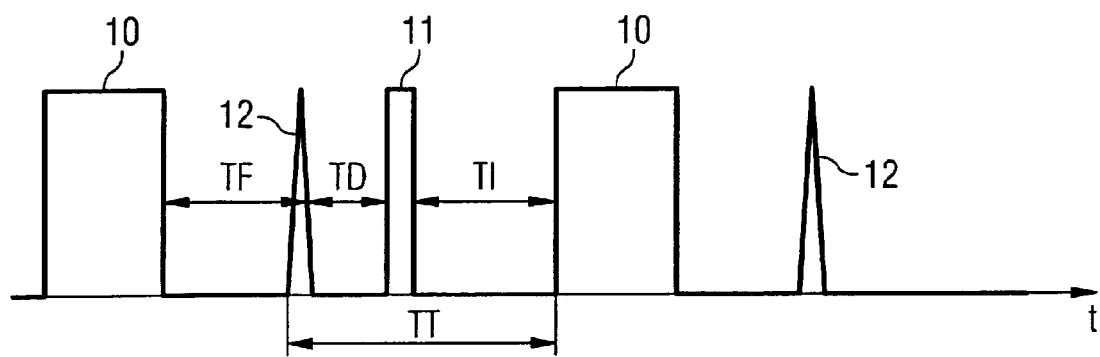
FIG. 1 illustrates a sequence for acquisition of MR images of the heart according to the invention.

A sequence diagram is schematically shown in FIG. 1. The acquisition of the MR signals ensues during the blocks 10. In one exemplary embodiment of the invention the imaging sequence is a spoiled gradient echo sequence with an inversion pulse that is schematically represented with reference character 11. The imaging sequence is a segmented imaging sequence, such that only N RF pulses with the flip angle α are respectively radiated during the blocks 10. As described in detail further below, the flip angles α are not constant, rather they become larger within a block 10. Furthermore, the R-spike 12 of the EKG signal is shown in FIG. 1. This R-spike serves as a trigger for the selection of the point in time for switching of the inversion pulse and the RF excitation pulses. The time spans shown in FIG. 1 are defined as follows. The time span TF is the fill time after the signal readout until the next R-spike. The time span TD runs from the R-spike until the switching of the RF inversion pulse 11. The inversion time TI is the point in time from the inversion pulse 11 until the signal readout. As is easily recognizable in FIG. 1, the connection between TT, TD and TI is as follows:

$$TT = TD + TI$$

The flip angle α of the imaging sequence is now varied within a segmented imaging section such that the transversal magnetization (which is responsible for the MR signal) of the blood is constant. The point in time for switching the inversion pulse is selected such that the longitudinal magnetization of the myocardium is zero at the signal readout. The greatest possible contrast between myocardium and blood located in the heart is hereby achieved in the MR image. The trigger delay for switching the inversion pulse corresponds to the time span TD. This delay, in which the myocardium exhibits no signal portions in the signal readout, can be calculated as follows:

$$TD(TF, TT) = T_1^M \cdot \ln\left[\frac{1 + \exp\left(-\frac{TF + TT}{T_1^M}\right)}{2}\right] + TT, \quad (1)$$

wherein $T_1^M$ designates the longitudinal relaxation time of the myocardium.

The longitudinal magnetization of the blood that is responsible for the signal is calculated as follows at the beginning of the signal readout $M_{z,0}^B$:

$$M_{z,0}^B = 1 - 2\exp\left(-\frac{TT - TD}{T_1^B}\right) + \exp\left(-\frac{TT + TD}{T_1^B}\right), \quad (2)$$

wherein $T_1^B$ designates the longitudinal relaxation time of the blood.

A constant flip angle that delivers a constant signal for all excitation pulses can be calculated as follows:

$$a_c = \arccos\left(\frac{1}{M_{z,0}^B}\left(1 - \frac{1 - M_{z,0}^B}{\exp\left(-\frac{TR}{T_1^B}\right)}\right)\right), \quad (3)$$

wherein TR designates the time between two excitation pulses.

According to an embodiment of the invention, the last excitation pulse is now set to α=90 degrees in order to achieve a maximum possible signal. The recursion formula for calculation of the preceding angles α now reads as follows:

$$M_T^n = M_z^n \cdot \sin(\alpha_n) = M_{z,0}^B \cdot \sin(\alpha_0), \quad (4)$$

wherein $M_T^n$ and $M_z^n$ designate the transversal or longitudinal magnetization of the blood in the n-th excitation pulse.

Furthermore, the following relationships apply:

$$\sin(\alpha_n) = \frac{M_{z,0}^B \sin(\alpha_0)}{1 = e\frac{TR}{T_1^B}\left(1 - \frac{M_{z,0}^B \sin(\alpha_0)}{\tan(\alpha_{n-1})}\right)} \quad (5)$$

$$\sin(\alpha_N) = 1, \text{ since } \alpha_N = 90°. \quad (6)$$

The recursion can be described as follows:

$$\alpha_{n-1} = \arctan\left[\frac{\exp\left(-\frac{TR}{T_1^B}\right)}{\frac{1}{\sin(\alpha_n)} + \frac{\exp\left(-\frac{TR}{T_1^B}\right) - 1}{M_{z,0}^B \cdot \sin(\alpha_0)}}\right] \quad (7)$$

Equation 7 gives the relationship between $\alpha_{N-1}$ and $\alpha_N$. An MR image with maximum signal contrast can be achieved with maximum signal contrast, wherein it is furthermore ensured that the signal of the blood remains constant during the signal acquisition.

A flowchart is shown in FIG. 2 with individual steps to achieve an optimal contrast in a contrast agent-supported heart imaging with inversion pulse. After the start of the method in step 21, the value TF (i.e. the fill time after the signal acquisition until the next R-spike) is determined from preceding heart cycles of the acquired EKG signal in a step 22. Furthermore, the value TT (i.e. the trigger delay for the imaging) is determined. This can be established as a constant; however, it is also possible to determine the value TT dependent on the pulse frequency. If the pulse frequency increases during the MR acquisition, the time span TT must shorten so that an imaging is possible during the rest phases of the heart. In a next the values TD and TI are then calculated with the equations 1 and 2 cited above (step 23). In a further step 24 the value $M_{z,0}^B$ is calculated with the aid of equation 2. Finally, the flip angle $\alpha_N$ is set equal to 90° in step 26, and the remaining flip angles of $\alpha_{N-1}$ through $\alpha_0$ are calculated with the aid of equation 7. This also yields a new $\alpha_0$. An average value of the previous start value $\alpha_0$ and the present start value $\alpha_0$ is calculated in step 28. Finally, in step 28 it is checked whether the difference is smaller than a predetermined threshold Δ. If this is not the case, the iteration is repeated. The method is ended only when the difference of the previous start flip angle and running start flip angle is smaller than the threshold Δ. For example, Δ can be selected between 0.1 and 1 degree. The method ends in step 29.

The present invention thus enables a contrast optimization and an improved spatial resolution by the calculation of the sequence parameters during the run time of the sequence.

Although modifications and changes may be suggested by those skilled in the art, it is the intention of the inventor to embody within the patent warranted hereon all changes and modifications as reasonably and properly come within the scope of his contribution to the art.

I claim as my invention:
1. A method for acquiring a magnetic resonance image of a heart comprising:
   administering contrast agent to a patient and, while the contrast agent is effective in the heart of the patient, controlling a magnetic resonance apparatus from a con- trol computer to acquire magnetic resonance signals from the heart by generating, and exposing the patient in the magnetic resonance apparatus to, a magnetic resonance imaging pulse sequence in successive cardiac cycles, including at least one pulse during which magnetic resonance signals from the heart are acquired, and including emitting a radio-frequency (RF) inversion pulse that inverts magnetization at least in the heart, at a point in time before said at least one pulse;

while acquiring said magnetic resonance signals, detecting a cardiac signal over a plurality of successive cardiac cycles of the heart, each of said cardiac cycles comprising an R-spike, said successive cardiac cycles, and thus said R-spike, being subject to a changing rate during said acquisition of said magnetic resonance signals;

providing said cardiac signal to said control computer and, in said control computer, for each respective cardiac cycle, among said successive cardiac cycles, in which said magnetic resonance data are acquired, determining a time span TF from an end of acquisition of said magnetic resonance signals of an immediately preceding cardiac cycle, and determining a time span TT from said R-spike of the respective cardiac cycle until a beginning of acquisition of magnetic resonance signals in the respective cardiac cycle, and calculating a time span TD after said R-spike in the respective cardiac cycle, dependent on TT and TF, thereby making TD dependent on said changing rate;

in each of said cardiac cycles in which said magnetic resonance signals are acquired, emitting said RF inversion pulse at an end of TD calculated for that respective cardiac cycle and thereby beginning acquisition of said magnetic resonance signals in the respective cardiac cycle at a time TI, following the R-spike in the respective cardiac cycle in which said magnetic resonance signals are acquired, that because TD is dependent on said changing rate, is also dependent on said changing rate, and that minimizes a longitudinal magnetization of the myocardium of the heart; and reconstructing an image that includes the myocardium of the heart from the magnetic resonance signals acquired during the respective cardiac cycle, and making the reconstructed magnetic resonance image available in electronic form as a data file.

2. A method as claimed in claim 1 comprising employing, as said imaging sequence, a segmenting imaging sequence in which data are entered only into a portion of k-space during a cardiac cycle of the heart in the imaging sequence.

3. A method as claimed in claim 1 comprising employing a gradient echo-based imaging sequence as said imaging sequence, with a bipolar gradient as said at least one pulse, and wherein only N RF excitation pulses are emitted during a cardiac cycle of the heart.

4. A method as claimed in claim 1 comprising calculating a magnetization of blood in the subject at a point in time of acquisition of said magnetic resonance signals.

5. A method as claimed in claim 1 comprising, during said imaging sequence, emitting a plurality of RF excitation pulses each having a flip angle, and varying the respective flip angles of the respective RF excitation pulses to make said magnetic resonance signals substantially constant.

6. A method as claimed in claim 1 comprising emitting N of said RF excitation pulses during a cardiac cycle of the heart, and varying the respective flip angles to give an Nth excitation pulse a flip angle of 90°, and iteratively calculating the respective flip angles for each preceding excitation pulse from the flip angle of the excitation pulse immediately following.

7. A method as claimed in claim 1 comprising injecting a contrast agent that interacts with the heart before acquiring said magnetic resonance signals.

* * * * *